United States Patent [19]

McCarthur

[11] 3,932,611

[45] Jan. 13, 1976

[54] HAIR DRESSING COSMETIC

[76] Inventor: Connie M. McCarthur, 3709 Lovingood Drive, Dallas, Tex. 75241

[22] Filed: Aug. 21, 1974

[21] Appl. No.: 499,270

[52] U.S. Cl. ............... 424/70; 424/DIG. 4; 424/74
[51] Int. Cl.² ............................................ A61K 7/06
[58] Field of Search ................... 424/70, 74, DIG. 4

[56] References Cited
UNITED STATES PATENTS

| | | | |
|---|---|---|---|
| 77,911 | 5/1868 | Peckham | 424/70 |
| 111,443 | 1/1871 | Fallis | 424/70 |
| 1,600,340 | 9/1926 | Kobbe | 424/70 X |

FOREIGN PATENTS OR APPLICATIONS

| | | | |
|---|---|---|---|
| 120,448 | 10/1945 | Australia | 424/70 |
| 126,210 | 12/1947 | Australia | 424/70 |
| 117,566 | 7/1918 | United Kingdom | 424/70 |
| 758,855 | 10/1956 | United Kingdom | 424/70 |
| 824,353 | 11/1959 | United Kingdom | 424/70 |

*Primary Examiner*—Albert T. Meyers
*Assistant Examiner*—Vera C. Clarke
*Attorney, Agent, or Firm*—Warren H. Kintzinger

[57] ABSTRACT

A composition for hair and scalp care and grooming comprised of white petroleum jelly, beeswax, coconut oil, olive oil, castor oil, oil of sassafras, and oil of cinnamon. The oil ingredients are mixed into petroleum jelly and beeswax that have been liquified by heating, and the entire mixture is cooled to form a uniform, congealed hair and scalp cosmetic preparation.

2 Claims, No Drawings

HAIR DRESSING COSMETIC

This invention relates in general to new compositions of matter, and in particular, to a mixture of substances useful in hair grooming and in the alleviation of dry hair and dry scalp problems.

Many commercially available cosmetics aid various hair care procedures and special problems, and the particularly desirable ones add sheen, luster, and body to the hair without leaving a waxy or greasy coating. A good hair cosmetic should impart oil moisture to the hair to prevent splitting and breaking ends that occur if the hair becomes very dry. A good hair cosmetic should also prevent atmospheric water vapor absorption, which usually releases the hair style setting.

Hair dressings that aid in suppressing the unattractive appearance of dandruff in the hair are widely known and used, and although dandruff is a natural occurrence on the scalp —that may be increased by skin and scalp conditions warranting medical treatment, hair care cosmetics are usually intended for widespread, individual consumer usage and the inclusion of controlled drug or chemical ingredients requiring medical prescriptions for consumer purchase is undesirable.

It is, therefore, a principal object of this invention to provide an improved hair dressing composition useful in normal hair grooming.

Another object is to provide a hair dressing composition that will retard the loss of hair moisture normally encountered during pressing, drying, and combing procedures.

A further object is to provide a dressing composition to soften hard, abused hair.

Another object is to provide a hair dressing composition useful in retarding dandruff's appearing in, and falling from, the hair.

The preferred embodiment, useful in accomplishing the above objects of this invention, is mixed from the following formula of ingredients:

| Ingredient | Common Measure | Per Cent by Volume |
| --- | --- | --- |
| White Petroleum Jelly | 9 lbs. | 86.808 |
| Beeswax (bleached) | 4 oz. (av.) | 2.192 |
| Olive Oil | 16 oz. (fl.) | 7.011 |
| Castor Oil | 6 oz. (fl.) | 2.631 |
| Coconut Oil | 3 oz. (fl.) | 1.316 |
| Sassaphras Oil | ⅛ tsp. | .024 |
| Cinnamon Oil | ¼ tsp. | .018 |

The composition is prepared by first heating the beeswax in a stainless steel container at low heat (200° – 220°F) until the beeswax liquifies. With the heat maintained within the same temperature range of 200° – 220°F, the petroleum jelly is added and gently agitated until it liquifies and blends with the beeswax. All of the remaining ingredients of the foregoing formula may then be added, and gentle agitation is continued until all ingredients are well blended. The container is then removed from the heat and the mixture is poured into distribution containers to cool (to less than 100°F) and congeal into a homogeneous mixture having a soft, smooth consistency slightly more viscous than petroleum jelly. The mixture maintains this consistency throughout the range of usual household ambient temperatures, with no separation or stratification of ingredients. Variations in the formula not amounting to more or less than fifteen percent of one or more of the ingredients do not materially affect the consistency of the hair dressing preparation. Greater variations may result in a consistency too hard, or too soft, for optimum consumer use—as well as affecting the homogeneous stability of the mixture.

Each ingredient serves a specific purpose that may be adversely affected by variation greater than the prescribed amount, plus or minus 15 percent of one or more ingredients. White petroleum jelly is the base material of the preparation, acting as a carrier for the other ingredients, as well as imparting softening moisture to the hair. As the base carrier material, the amount of petroleum jelly controls the relative concentration of the active ingredients. Beeswax, also a base material, thickens and adds body to the petroleum jelly base and facilitates hair style control and maintenance because of the viscosity it imparts to the mixture. The petroleum jelly, beeswax and, to a lesser extent, the oil ingredients act to protect hair from atmospheric moisture adsorption—a common cause of uncontrollable hair. Olive oil and coconut oil are used in the formulation of the invention for their emollient effects on the hair and scalp. Olive oil also promotes healing of minor scalp irritations and abrasions. A soft gloss, often considered the outward indication of healthy, natural hair, is produced by the use of castor oil in the preparation. Oil of sassaphras is an astingent that stimulates the scalp and the hair roots and follicles. Oil of cinnamon is used as a preferred perfuming agent, but other perfuming agents may be substituted to obtain fragrance variations.

The composition of the invention is normally used by applying a small amount to the hair and scalp preparatory to setting, pressing, or dressing. Hair stylings and set curls are retained by the effects of the composition, in a manner that gives the hair a naturally resilient texture and appearance, rather than the rigidly set-in-place appearance, especially after combing. Individual hair strands are surrounded with a softening, oily moisture that complements the natural secretions of the hair follicles which contribute to soft and controllable hair. The beeswax of the mixture has a slight stiffening effect sufficient to materially aid in holding set curls and stylings without suppressing the natural resiliency of the hair, with the added benefit that the mixture prevents adsorption of atmospheric water vapor on the hair, which causes a release of set curls and stylings.

Because of the oily nature of the mixture, loose dandruff particles are held in close proximity to the scalp, preventing the unsightly appearance of dandruff particles in the hair or on clothing. The suspended dandruff particles are washed away with the mixture of the invention, in regular shampooing.

Whereas the invention is herein described with respect to a preferred embodiment, it should be realized that various changes may be made without departing from the essential contributions to the art made by the teachings hereof.

I claim:

1. A uniform hair and scalp care cosmetic mixture, comprised of volumetric proportional ingredients, with any one ingredient not exceeding a 15 percent volumetric variation from the specific ingredients, and percentages of total mixture volume thereof defined by and proportional to 86.808 percent white petroleum jelly, 2.129 percent beeswax, 7.011 percent olive oil, 2.631 percent castor oil, 1.316 percent coconut oil, 0.024 percent oil of sassaphras, and 0.018 percent perfuming agent; said mixture having a consistency slightly more viscous than petroleum jelly.

2. The cosmetic mixture of claim 1, wherein said perfuming agent is oil of cinnamon.

* * * * *